(12) United States Patent
Frater et al.

(10) Patent No.: US 10,071,950 B2
(45) Date of Patent: Sep. 11, 2018

(54) USE OF IMMOBILIZED MOLYBDENUM- AND TUNGSTEN-CONTAINING CATALYSTS IN OLEFIN CROSS METATHESIS

(71) Applicant: XiMo AG, Horw/Lucerne (CH)

(72) Inventors: Georg Emil Frater, Horw/Lucerne (CH); Jeno Varga, Horw/Lucerne (CH); Christophe Coperet, Zurich (CH); Emmanuel Robe, Horw/Lucerne (CH); Victor Mougel, Zurich (CH)

(73) Assignee: XIMO AG, Horw/Lucerne (CH)

( * ) Notice: Subject to any disclaimer, the term of this patent is extended or adjusted under 35 U.S.C. 154(b) by 0 days.

(21) Appl. No.: 14/903,119

(22) PCT Filed: Jul. 11, 2014

(86) PCT No.: PCT/EP2014/001909
§ 371 (c)(1),
(2) Date: Jan. 6, 2016

(87) PCT Pub. No.: WO2015/003814
PCT Pub. Date: Jan. 15, 2015

(65) Prior Publication Data
US 2016/0159727 A1    Jun. 9, 2016

(30) Foreign Application Priority Data
Jul. 12, 2013   (EP) .................................... 13003541

(51) Int. Cl.
| | | |
|---|---|---|
| *C07C 67/293* | (2006.01) | |
| *B01J 23/28* | (2006.01) | |
| *B01J 23/30* | (2006.01) | |
| *C07F 11/00* | (2006.01) | |
| *C07C 6/04* | (2006.01) | |
| *B01J 37/02* | (2006.01) | |
| *C11C 3/00* | (2006.01) | |
| *C11C 3/14* | (2006.01) | |
| *B01J 31/18* | (2006.01) | |

(52) U.S. Cl.
CPC ............ *C07C 67/293* (2013.01); *B01J 23/28* (2013.01); *B01J 23/30* (2013.01); *B01J 31/1805* (2013.01); *B01J 37/0209* (2013.01); *C07C 6/04* (2013.01); *C07F 11/00* (2013.01); *C11C 3/00* (2013.01); *C11C 3/14* (2013.01); B01J 2231/543 (2013.01); B01J 2531/64 (2013.01); B01J 2531/66 (2013.01); C07C 2531/22 (2013.01); C07C 2531/34 (2013.01)

(58) Field of Classification Search
CPC ................................................... C07C 67/293
See application file for complete search history.

(56) References Cited

U.S. PATENT DOCUMENTS

| | | |
|---|---|---|
| 3,696,161 A | 1/1972 | Kobetz et al. |
| 4,637,197 A | 1/1987 | Banfield et al. |
| 5,378,783 A | 1/1995 | Okumura et al. |
| 6,121,473 A | 9/2000 | Schrock et al. |
| 8,993,470 B2 | 3/2015 | Fuerstner et al. |
| 9,079,173 B2 | 7/2015 | Schrock et al. |
| 2003/0135080 A1 | 7/2003 | Botha et al. |
| 2005/0107529 A1 | 5/2005 | Datta et al. |
| 2005/0124839 A1 | 6/2005 | Gartside et al. |
| 2008/0119678 A1 | 5/2008 | Hock et al. |
| 2011/0015430 A1 | 1/2011 | Schrock et al. |
| 2011/0077421 A1 | 3/2011 | Schrock et al. |
| 2011/0160472 A1 | 6/2011 | Lemke et al. |
| 2011/0263917 A1 | 10/2011 | Van Hal et al. |
| 2012/0316057 A1 | 12/2012 | Taoufik et al. |
| 2013/0006012 A1 | 1/2013 | Firth et al. |
| 2013/0035502 A1 | 2/2013 | Cohen et al. |
| 2013/0144102 A1 | 6/2013 | Fuerstner et al. |
| 2013/0217906 A1 | 8/2013 | Kunz et al. |
| 2014/0275595 A1 | 9/2014 | Wampler et al. |
| 2014/0309466 A1 | 10/2014 | Ondi et al. |
| 2016/0030936 A1 | 2/2016 | Ondi et al. |
| 2016/0122375 A1 | 5/2016 | Coperet et al. |

FOREIGN PATENT DOCUMENTS

| | | |
|---|---|---|
| EP | 0116408 | 1/1984 |
| EP | 0534388 A1 | 3/1993 |
| EP | 0864595 A1 | 9/1998 |
| EP | 2703081 A1 | 3/2014 |
| WO | 2008066754 | 6/2008 |
| WO | 2009094201 A1 | 7/2009 |
| WO | 2011007742 A1 | 1/2011 |
| WO | 2011097642 A1 | 8/2011 |

OTHER PUBLICATIONS

Meek, et al. Nature, 471, Mar. 24, 2011, pp. 461-466.*
Arndt, et al., "Synthesis and Reactions of Tungsten Alkylidene Complexes that Contain the 2,6-Dichlorophenylimido Ligand", Organometallics, 26, 2007, 1279-1290.
Bindl, et al., "Molybdenum Nitride Complexes with Ph3SiO Ligands are Exceedingly Practical And Tolerant Precatalysts for Alkyne Metathesis and Efficient Nitrogen Transfer Agents", J Am Chem Soc., 1321(27), Jul. 15, 2009, 9468-9470.
Dolman, et al., "Enantioselective Synthesis of Cyclic Secondary Amines through Mo-Catalyzed Asymmetric Ring-Closing Metathesis (ARCM)", Organic Letters col. 5, No. 25, 2003, pp. 4899-4902.
Flook, et al., "Z-Selective and Syndioselective Ring-Opening Metathesis Polymerization (ROMP) Initiated by Monoaryloxidepryrrolide (MAP) Catalysts", Macromolecules vol. 43 No. 18, 2010, pp. 7515-7522.

(Continued)

*Primary Examiner* — Shawquia Jackson
(74) *Attorney, Agent, or Firm* — Stoel Rives LLP

(57) ABSTRACT

Method of forming an olefin from a first olefin and a second olefin in a metathesis reaction, comprising step (i): (i) reacting the first olefin with the second olefin in the presence of a silica supported Mo- or W-alkylidene catalyst, wherein the first olefin and the second olefin are different from one another.

13 Claims, No Drawings

(56) References Cited

OTHER PUBLICATIONS

Jiang, et al., "Fundamental Studies of Tungsten Alkylidene Imido Monoalkoxidepyrrolide Complexes", J. Am. Chem. Soc. vol. 131, 2009, pp. 7770-7780.
Malcolmson, et al., "Highly efficient molybdenum-based catalysts for enantioselective alkene metathesis", Nature, vol. 456, Dec. 25, 2008, pp. 933-937.
Marinescu, et al., "Syntheses of Variations of Stereogenic-at-Metal Imido Alkylidene Complexes of Molybdenum", Organometallics, vol. 31 No. 17, 2012, pp. 6336-6343.
Mazoyer, et al., "Development of the First Well-Defined Tungsten Oxo Alkyl Derivatives Supported on Silica by SOMC: towards a Model Of WO3/SiO2 Olefin Metathesis Catalyst", Chem. Commun., 46, 2010, 8944-8946.
Merle, et al., "On the Track to Silica-Supported Tungsten Oxo Metathesis Catalysts: Input from O Solid-State NMR", Inorg. Chem., 52, 2013, 10119-10130.
Oskam, et al., "Rational Isomers of Mo(VI) Alkylidene Complexes and Cis/Trans Polymer Structure: Investigations in Ring-Opening Metathesis Polymerization", J. Am. Chem. Soc. 115, 1993, pp. 11831-11845.
PCT/EP2014/002654, International Search Report and Written Opinion, dated Dec. 17, 2014, 10 pages.
Peryshkov, et al., "Synthesis of Tungsten Oxo Alkylidene Complexes", Organometallics, 31, 2012, 7278-7286.
Peryshkov, et al., "Z-Selective Olefin Metathesis Reactions Promoted by Tungsten Oxo Alkulidene Complexes", JACS, 133, 2011, pp. 20754-20757.
Rhers, et al., "A Well-Defined, Silica-Supported Tungsten Imido Alkylidene Olefin Metathesis Catalyst", Organometallics, 25, 2006, 3554-3557.
Schrock, et al., "Further Studies of Imido Alkylidene Complexes of Tungsten, Well-Characterized Olefin Metathesis Catalysts with Controllable Activity", Organometallics, 9(8), 1990, 2262-2275.
Schrock, "High Oxidation State Multiple Metal-Carbon Bonds", Chem Rev., 102, 2002, 145-179.
Schrock, "Multiple Metal-Carbon Bonds for Catalytic Metathesis Reactions (Nobel Lecture)", Angew Chem Int Ed Engl, 45(23), 2006, 3748-3759.
Schrock, et al., "Recent Advances in the Syntheses and Applications of Molybdenum and Tungsten Alkylidene and Alkylidene Catalysts for the Metathesis of Alkenes and Alkynes", Adv Sys Catal., 349, 2007, 55 pages.
Singh, et al., "Synthesis of Monoalkoxide Monopyrrolyl Complexes Mo(NR)(CHR')(OR")(pyrrolyl) Enyne Metathesis with High Oxidation State Catalysts", J. Am. Chem. Soc. 129, 2007, pp. 12654-12655.
Yuan, "Pentafluorophenylimido Alkylidene Complexes of Molybdenum and Tungsten", Organometallics, vol. 31, 2012, pp. 4650-4653.
Office Action dated Feb. 10, 2017 for U.S. Appl. No. 14/209,313.
Blanc, et al., "Dramatic Improvements of Well-Defined Silica Supported Mo-Based Olefin Metathesis Catalysts by Tuning the N-Containing Ligands", J Am Chem Soc., 129(27), 2007, 8434-8435.
Blanc, et al., "Highly Active, Stable, and Selective Well-Defined Silica Supported Mo Imido Olefin Metathesis Catalysts", J Am Chem Soc., 129(17), 2007, 1044-1045.
Blanc et al., 'Dramatic Improvements of Well-Defined Silica Supported Mo-Based Olefin Metathesis Catalysts by Tuning the N-Containing Ligands', JACS 2007, vol. 129 No. 27, pp. 8434-8435.
European Search Report dated Nov. 25, 2013 for EP13003541.3.
International Search Report and Written Opinion dated Aug. 7, 2014 for PCT/EP2014/001909.
Rendon et al., 'Well-Defined Silica-Supported No-Alkylidene Catalyst Precursors Containing One or Subsitituent: Methods of Preparation and Structure-Reactivity Relationship in Alkene Metathesis', Chem. Euro. J., 2009, 15, pp. 5083-5089.
U.S. Appl. No. 13/639,067, Notice of Allowance, dated Jan. 21, 2015, 19 pages.
13001297.4, Extended European Search Report, dated Nov. 6, 2013.
U.S. Appl. No. 14/001,811, Non-Final Office Action, dated Jun. 30, 2015, 14 pages.
U.S. Appl. No. 14/001,811, Notice of Allowance, dated Oct. 9, 2015, 5 pages.
U.S. Appl. No. 14/011,811, Office Action, dated Oct. 9, 2015.
Allen, et al., "Preparation of High Purity, Anionic Polymerization Grade Alkyl Mathacrylate Monomers", Polymer Bulletin, 15, 1986, pp. 127-134.
Bailey, et al., "Evaluation of Molybdenum and Tungsten Metathesis Catalysts for Homogeneous Tandem Alkane Metathesis", Organometallics, 28, 2009, pp. 355-360.
Blanc, et al., "Direct Observation of Reaction Intermediates for a Well Defined Heterogeneous Alkene Metathesis Catalyst", PNAS, vol. 105 No. 34, Aug. 26, 2008, pp. 12123-12127.
Blanc, et al., "Highly Active, Stable, and Selective Well-Defined Silica Supported Mo Imido Olefin Metathesis Catalysts", J. Am. Chem. Soc., 129, 2007, pp. 1044-1045.
EP13003540.5, Extended European Search Report, dated Dec. 11, 2013.
Fox, et al., "Synthesis of Five-and Six-Coordinate Alkylidene Complexes of the Type Mo (CHR) (NAr) [OCMe (CF3) 2Sx and Their Use as Living ROMP Initiators or Wittig Reagents", American Chemical Society, Organometallics, 12, 1993, pp. 759-768.
Heppekausen, et al., "Practical New Silyloxy-Based Alkyne Metathesis Catalysts with Optimized Activity and Selectivity Profiles", J Am Chem Soc., vol. 132 No. 32, 2010, pp. 11045-11057.
Heppekausen, et al., "Rendering Schrock-type Molybdenum Alkylidene Complexes Air Stable: User-Friendly Precatalysts for Alkene Metathesis", Angewandte Chemie (International Ed.) vol. 123, No. 34, Aug. 16, 2011, pp. 7975-7978.
Jiang, et al., "Highly Z-Selective Metathesis Homocoupling of Terminal Olefins", J. Am. Chem. Soc. 131, 2009, pp. 16630-16631.
Lee, et al., "Endo-Selective Enyne Ring-Closing Metathesis Promoted by Stereogenic-at-Mo Monoalkoxide and Monoaryloxide Complexes. Efficient Synthesis of Cyclic Dienes Not Accessible Through Reactions with Ru Carbines", J Am Chem Soc., 131(30), Aug. 5, 2009, 10652-10661.
Marinescu, et al., "Ethenolysis Reactions Catalyzed by Imido Alkylinene Monoaryloxide Monopyrrolide (MAP) Complexes of Molybdenum", Journal of the American Chemical Society, ACS Publications, US, vol. 131 No. 31, Aug. 12, 2009, 10840-10841.
Marinescu, et al., "Simple Molybdenum (IV) Olefin Complexes of the Type Mo(NR)(X)(Y)(olefin)", Organometallics, 29, 2010, pp. 6816-6828.
PCT/DE2011/000348, International Search Report and Written Opinion with English Translation, dated Jul. 22, 2011, 10 pages.
PCT/DE2011/000348, International Preliminary Report on Patentability, dated Oct. 9, 2012, 5 pages.
PCT/DE2012/100047, International Search Report and Written Opinion (with English translation), dated Jul. 24, 2012, 10 pages.
PCT/DE2012/100047, International Preliminary Report on Patentability, dated Sep. 3, 2013, 6 pages.
PCT/EP2014/000671, International Search Report and Written Opinion, dated Dec. 16, 2014.
PCT/EP2014/001910, International Search Report and Written Opinion, dated Sep. 24, 2014.
Schrock, "Recent Advances in High Oxidation State Mo and W Imido Alkylidene Chemistry", Chemical Reviews, vol. 109 No. 8, Mar. 13, 2009, pp. 3211-3226.
Totland, et al., "Ring Opening Metathesis Polymerization with Binaphtholate or Bibhenolate Complexes of Molybdenum", American Chemical Society, Macromolecules, 29, 1996, pp. 6114-6125.
Tsai, et al., "Facile Synthesis of Trialkoxymolybdenum(VI) Alkylidyne Complexes for Alkyne Metathesis", Organometallics, 19, 2000, 5260-5262.
Yu, et al., "Enol Ethers as Substrates for Effecient Z- and Enentioselective Ring-Opening/Cross-Metathesis Reactions Promoted by Sterogenisat-Mo Complexes: Utility in Chemical Synthesis and Mechanistice Atrributes", J. Chem. Soc., 134, 2012, 2788-2799.
Yu, et al., "Synthesis of Macrocyclic Natural Products by Catalyst-Controlled Stereoselective Ring-Closing Metathesis", Nature, vol. 479 No. 7371, Nov. 2, 2011, pp. 89-93.

(56) References Cited

OTHER PUBLICATIONS

Blanc, et al., Surface versus Molecular Siloxy Ligands in Well-Defined Olefin Metathesis Catalysts: [{(RO)3SiO}Mo (=NAr)(=CHtBu)(CH2tBu)], Angew. Chem. Int. Ed. 2007, 45, 1216-1220.
Chabanas, et al., A Highly Active Well-Defined Rhenium Heterogenous Catalyst for Olefin Metathesis Prepared via Surface Organometallic Chemsitry, J. Am Chem Soc. 2001, 123, 2062-2063.
Jiang, et al., Highly Z-Selective Metathesis Homocoupling of Terminal Olefins, J Am Chem Soc., 131(46) ,2009 ,16630-16631.
Malcolmson, et al., Highly Efficient Molybdenum-Based Catalyst for Enantioselective Alkene Metathesis, Nature, 456(7224), Epub Nov. 16, 2008 ,Dec. 18, 2008 ,933-937.
Solans-Monfort, et al., d0 Based Olefin Metathesis Catalysts, Re(=CR)(=CHR)(X)(Y): The Key Role of X and Y Ligands for Efficient Active Sites, J. Am. Chem. Soc. 2005, 127 14015-14025.
Wang, et al., Molybdenum-Based Complexes with Two Aryloxides and a Pentafluoroimido Ligand: Catalysts for Efficient Z-Selective Synthesis of a Macrocyclic Trisubstituted alkene by Ring-Closing Metathesis, Angew Chem Int Ed Engl, 52(7) ,2013 ,1939-1943.
Office Action dated Mar. 24, 2017 for U.S. Appl. No. 14/774,404.
Office Action dated Aug. 24, 2017 for U.S. Appl. No. 14/209,313.
Notice of Allowance dated Nov. 2, 2017 for U.S. Appl. No. 14/774,404.

* cited by examiner

USE OF IMMOBILIZED MOLYBDENUM- AND TUNGSTEN-CONTAINING CATALYSTS IN OLEFIN CROSS METATHESIS

The invention relates to immobilized molybdenum and tungsten catalysts. Said catalysts may be used in olefin cross metathesis.

Due to the growing importance of olefin cross metathesis between two different olefins, e.g. ethenolysis of an olefin, a great need exists for the provision of appropriate methods which can be beneficially carried out at an industrial scale. In particular, the manufacture of propylene starting from 2-butene and ethylene is of particular importance due to the growing importance of propylene as starting material for many industrial processes.

US 2012/0316057 relates to a tungsten catalyst comprising a tungsten metal compound which contains a least one tungsten-fluorine bond, the compound being dispersed on a refractory oxide support, wherein the compound is chemically bonded to the support. Said catalyst may be employed in the metathesis reaction of 2-butene and ethylene to produce propylene.

N. Rendon et. al., Chem. Eur. J. 2009, 15, 5083-5089, disclose silica supported Mo-alkylidene catalysts containing one OR substituent which may be used in olefin metathesis reactions.

F. Blanc et al., J. Amer. Chem. Soc. 2007, 129, 8434-8435, disclose silica supported Mo-alkylidene catalysts containing a pyrrolide substituent which can be used in an olefin metathesis reaction.

One object to be achieved by the present invention is the provision of a method for performing cross metathesis between two different olefins which beneficially can be carried out at an industrial scale.

This object is achieved with a method in which the metathesis between two different olefins is catalyzed by means of immobilized molybdenum-alkylidene or tungsten-alkylidene catalysts. Contrary to homogeneous catalysis, where the catalyst frequently has to be separated off by a rather complex processing of the reaction mixture, whereby the catalyst often is destroyed or at least considerably deteriorated in its activity, the catalysts employed in the process according to the invention may be separated off from the reaction mixture via simple processing, e.g. by filtration or centrifugation. The catalysts may be re-used in olefin metathesis. This is particularly beneficial at an industrial scale.

The method according to the invention differs from the known use of silica supported Mo-alkylidene catalysts containing one OR substituent. This prior art discloses heterogeneously catalyzed olefin homo or self metathesis (SM) and ring closing metathesis (RCM) (N. Rendon et. al., Chem. Eur. J. 2009, 15, 5083-5089) whereas the subject method relates to a cross metathesis reaction between two different olefins. The method according to the invention also differs from the known use of Mo-alkylidene catalysts containing a pyrrolide substituent. This prior art discloses self metathesis (SM) of propene (F. Blanc et al., J. Amer. Chem. Soc. 2007, 129, 8434-8435) whereas the subject method relates to a cross metathesis reaction between two different olefins. Since the structure of the catalysts used in the present invention has an alkylidene group and the structure of the catalysts disclosed in US 2012/0316057 is free of an alkylidene group, said catalysts are different from one another.

In a first aspect, the invention relates to a method of forming an olefin from a first olefin and a second olefin in a metathesis reaction, comprising at least step (i):
  (i) reacting the first olefin with the second olefin in the presence of a silica supported Mo-alkylidene or W-alkylidene catalyst,
wherein the first olefin and the second olefin are different from one another.

Preferably, the method according to step (i) is carried out in a solvent, which dissolves the olefins and suspends the catalyst. Suitable solvents are solvents selected from aromatics, preferably toluene, halogenated solvents, preferably chlorobenzene or methylene dichloride, alkanes, preferably pentane or hexane or octane. However, step (i) may be carried out without solvent, preferably if one of the olefins is a liquid under the reaction conditions. However, the reaction may also be carried out such that the first olefin and the second olefin are in gaseous phase or the first olefin is gaseous and the second olefin is in liquid phase.

The temperature employed in step (i) preferably ranges from −20° C. to 200° C., more preferably from 0° C. to 110° C., still more preferably from 15 to 50° C.

The concentration of the catalyst can vary in broad ranges. Preferably, the catalyst is employed in a molar ratio of <5 mole % (calculated in terms of W or Mo), based on the first or the second olefin (100 mole %).

The cross metathesis (CM) between the first and the second olefin may be carried out with various types of olefins.

Preferably,
  (a) the first olefin is a cyclic olefin and the second olefin is a cyclic olefin; or
  (b) the first olefin is a cyclic olefin and the second olefin is a non-cyclic olefin; or
  (c) the first olefin is a non-cyclic olefin and the second olefin is a non-cyclic olefin.

Preferably, the first olefin or the second olefin is a $C_4$-$C_{30}$ olefin.

The inventors of the present invention have discovered that the method according to the invention may be particularly advantageously employed as ethenolysis. Accordingly, the first olefin and the second olefin are a $C_4$-$C_{30}$ olefin and ethylene.

Thus, in a preferred embodiment, the first olefin has an internal olefinic double bond and the second olefin is ethylene. The olefin subjected to ethenolysis may be a cyclic or a non-cyclic olefin.

Most preferably, the first olefin is 2-butene and the second olefin is ethylene. Thus, the method according to the invention can be used for the manufacture of propylene using 2-butene and ethylene as starting materials.

The proceeding of the reaction may be preferably controlled by gas chromatographic methods.

Preferably, the reaction is terminated by separating off the catalyst from the reaction mixture obtained in step (i). Preferably, separating off may be performed by methods such as filtration or centrifugation or by distilling olefin off. The thus recovered catalyst may be re-used in step (i).

Accordingly, in one embodiment, the method according to the invention further comprises at least step (ii) or step (ii) and step (iii):
  (ii) separating off the catalyst from the reaction mixture obtained in step (i), preferably by filtration or centrifugation;
  (iii) re-using in step (i) the catalyst obtained in step (ii).

The silica-supported Mo- and W-alkylidene catalysts which can be employed in the method according to the invention are either known or may be prepared according to known methods, e.g. according to the method as described above in N. Rendon et. al., Chem. Eur. J. 2009, 15, 5083-5089.

Preferably, the catalyst used in the reaction according to the invention is of formula I

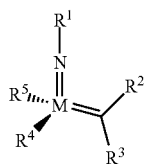

wherein

M is W or Mo;

$R^1$ is H, aryl, heteroaryl, alkyl, or heteroalkyl, optionally substituted, respectively;

$R^2$ and $R^3$ can be the same or different and are hydrogen, alkyl, alkenyl, heteroalkyl, heteroalkenyl, aryl, or heteroaryl, optionally substituted, respectively;

$R^5$ is a residue $R^6$—X—, wherein $R^6$ is alkyl, aryl, heteroalkyl, or heteroaryl, optionally substituted, respectively; ($R^7$, $R^8$, $R^9$)Si, wherein $R^7$, $R^8$, $R^9$ are independently alkyl, alkoxy, phenyl or phenoxy, optionally substituted, respectively; ($R^{10}$, $R^{11}$, $R^{12}$)C, wherein $R^{10}$, $R^{11}$, $R^{12}$ are independently phenyl or alkyl, optionally substituted, respectively;

X=O, S, or $NR^{13}$, wherein $R^{13}$ is H; or alkyl or aryl, optionally substituted, respectively; or $R^5$ is $R^6$—CO—$NR^{13}$, wherein $R^6$ and $NR^{13}$ have the meaning as defined above, or wherein $R^6$ and $R^{13}$ taken together form a carbon chain having from 2 to 6 carbon atoms;

$R^5$ is a 4 to 8 membered N-containing ring, preferably a carbon ring, wherein N is linked to M; and $R^4$ is a residue O—Si(O—)$_3$, and represents silica to which M is linked forming a M-O—Si(O—)$_3$ moiety, preferably wherein silica is comprised in a solid support.

In one embodiment, a catalyst of formula I is provided in which $R^1$ is aryl or adamant-1-yl, optionally substituted, respectively; preferably wherein $R^1$ is phenyl or naphthyl, or phenyl or naphthyl substituted with up to five substituents independently selected from $C_1$-$C_4$ alkyl, $C_1$-$C_4$ alkoxy, $CF_3$, F, Cl, Br, or phenyl or phenoxy, optionally substituted, respectively;

$R^2$ is —C(CH$_3$)$_2$C$_6$H$_5$ or —C(CH$_3$)$_3$;

$R^3$ is H;

$R^5$ is a residue $R^6$—X—, wherein

X=O and $R^6$ is phenyl or phenyl substituted with up to five substituents independently selected from alkyl, preferably $C_1$-$C_4$ alkyl, such as methyl, isopropyl or t-butyl; alkoxy, preferably $C_1$-$C_4$ alkoxy; phenoxy, phenyl, optionally substituted, respectively; or halogen; or X=S and $R^6$ is phenyl substituted with up to five substituents independently selected from alkyl, preferably $C_1$-$C_4$ alkyl such as methyl, isopropyl or t-butyl; alkoxy, preferably $C_1$-$C_4$ alkoxy; phenoxy, phenyl, optionally substituted, respectively; or halogen; or X=O and $R^6$ is triphenylsilyl or triphenoxysilyl, optionally substituted, respectively; or tri($C_1$-$C_4$ alkyl)silyl or tri($C_1$-$C_4$ alkoxy)silyl;

X=O and $R^6$ is triphenylmethyl, optionally substituted; or

X=O and $R^6$ is 9-phenyl-fluorene-9-yl; or

X=O and $R^6$ is 2-phenyl-1,1,1,3,3,3-hexafluoro-prop-2-yl [(C$_6$H$_5$)(CF$_3$)$_2$C]; or X=O and $R^6$ is t-butyl, optionally substituted with one or more F groups, preferably (CF$_3$)(CH$_3$)$_2$C, (CF$_3$)$_2$(CH$_3$)C, (CF$_3$)$_3$C.

In a preferred embodiment, $R^2$ is —C(CH$_3$)$_2$C$_6$H$_5$.

In another embodiment, a catalyst of formula I is provided in which $R^1$ is phenyl substituted with up to five substituents independently selected from $C_1$-$C_4$ alkyl, $C_1$-$C_4$ alkoxy, $CF_3$, F, Cl, Br, or phenyl or phenoxy, optionally substituted, respectively; and X=O and $R^6$ is phenyl or phenyl substituted with up to five substituents independently selected from $C_1$-$C_4$ alkyl, $C_1$-$C_4$ alkoxy, phenoxy, phenyl, halogen; or X=S and $R^6$ is phenyl or phenyl substituted with up to five substituents independently selected from $C_1$-$C_4$ alkyl, $C_1$-$C_4$ alkoxy, phenoxy, phenyl, halogen; or X=O and $R^6$ is triphenylsilyl, triphenoxysilyl, tri($C_1$-$C_4$ alkyl)silyl or tri($C_1$-$C_4$ alkoxy)silyl; or X=O and $R^6$ is t-butyl or t-butyl substituted with one or more F groups, preferably (CF$_3$)(CH$_3$)$_2$C, (CF$_3$)$_2$(CH$_3$)C, (CF$_3$)$_3$C; or (C$_6$H$_5$)(CF$_3$)$_2$C; or $R^5$ is pyrrol-1-yl, 2,5-dimethylpyrrol-1-yl, or 2,5-diphenylpyrrol-1-yl.

The inventors of the present invention have surprisingly discovered that the efficacy of the catalyst used in the method according to the invention may be further enhanced by a purposive selection of the residues $R^1$ and $R^5$.

Accordingly, in one preferred embodiment, a catalyst of formula I is provided in the method according to the invention in which $R^1$ is an electron donating group and $R^5$ is an electron withdrawing group.

Preferably, a catalyst is provided in which $R^1$ is phenyl substituted with up to five substituents independently selected from $C_1$-$C_4$ alkyl, $C_1$-$C_4$ alkoxy, phenyl, phenoxy;

$R^2$ is —C(CH$_3$)$_2$C$_6$H$_5$ or —C(CH$_3$)$_3$;

$R^3$ is H;

$R^5$ is (CF$_3$)(CH$_3$)$_2$CO, (CF$_3$)$_2$(CH$_3$)CO, (CF$_3$)$_3$CO, (C$_6$H$_5$)(CF$_3$)$_2$CO, pyrrol-1-yl, 2,5-dimethylpyrrol-1-yl, or 2,5-diphenylpyrrol-1-yl.

Preferably, $R^1$ is 2,6-diisopropylphenyl.

The inventors have further discovered that the object is also achieved if $R^1$ is an electron withdrawing group and $R^5$ is an electron donating group.

Preferably, a catalyst of formula I is provided in which $R^1$ is phenyl substituted with up to five substituents independently selected from CF$_3$, F, Cl, Br;

$R^2$ is —C(CH$_3$)$_2$C$_6$H$_5$ or —C(CH$_3$)$_3$;

$R^3$ is H;

$R^5$ is (CH$_3$)$_3$CO, tri($C_1$-$C_4$)silyloxy, or tri(phenyl)silyloxy; or phenoxy or phenylthio, wherein the phenyl moiety may be substituted with up to five substituents independently selected from $C_1$-$C_4$ alkyl, $C_1$-$C_4$ alkoxy, phenoxy, phenyl, halogen.

Preferably, $R^1$ is 2,6-dichlorophenyl, pentafluorophenyl, 2-(trifluoromethyl)phenyl or 2,6-di(trifluoromethyl)phenyl.

Catalysts in which both $R^1$ and $R^5$ are electron withdrawing groups may also be used in the method according to the invention.

Compounds in which both $R^1$ and $R^5$ are electron withdrawing groups preferably may have a structure in which $R^1$ is phenyl substituted with up to five substituents independently selected from $CF_3$, F, Cl, Br;

$R^2$ is $—C(CH_3)_2C_6H_5$ or $—C(CH_3)_3$;

$R^3$ is H;

$R^5$ is $(CF_3)(CH_3)_2CO$, $(CF_3)_2(CH_3)CO$, $(CF_3)_3CO$, $(C_6H_5)(CF_3)_2CO$, pyrrol-1-yl, 2,5-dimethylpyrrol-1-yl, or 2,5-diphenylpyrrol-1-yl.

Preferably, $R^1$ is 2,6-dichlorophenyl, pentafluorophenyl, 2-(trifluoromethyl)phenyl or 2,6-di(trifluoromethyl)phenyl.

The compounds of formula I used in the method according to the invention may be prepared by grafting appropriate precursor compounds on silica or on a support comprising silica.

Preferably, a silca is used which is partially dehydrated or dehydroxylated.

Preferably, silica is dehydroxylated and dehydrated at elevated temperature, preferably at elevated temperature and in vacuo.

Preferably, silica is dehydroxylated and dehydrated at 700° C. ($SiO_{2-(700)}$). However, other temperatures or temperature ranges may also be used depending on the requirements of the compound of formula I to be used as heterogeneous catalyst.

Suitable precursor compounds are e.g. compounds of formula I in which $R^4$ is a ligand that can be replaced by a O—Si(O—)$_3$ moiety. Suitable ligands are preferably alkoxy and 2,5-dimethylpyrrol-1-yl ligands. Suitable precursor compounds are known or may be prepared according to known methods.

According to a second aspect, the invention relates to the use of a silica supported Mo- or W-alkylidene catalyst as defined in the first aspect in an olefin cross metathesis between a first olefin and a second olefin, wherein the first and the second olefin are different from one another.

Preferably, said cross metathesis reaction is ethenolysis.

Definitions as Used in the Meaning of the Invention

The catalyst according to the invention is heterogeneous, i.e. it comprises a solid support. Said solid support comprises silica or consists of "silica".

A solid support may be any material that includes silica such as silica as such or silica in combination with other materials. Accordingly, silica may be used in the form of a mixed oxide, e.g. a mixed oxide of silica and alumina or silica and zirconia. Preferably, silica is used as such as solid support.

The term "silica" further encompasses porous or non-porous silica.

The term further encompasses partially dehydroxylated and/or dehydrated silica. Dehydroxylation and/or dehydration may be performed using elevated temperature or elevated temperature and vacuum. Residual hydroxyl content may be determined by titration with MeMgCl.

Hydroxyl content may be freely selected depending on drying temperature and drying time. Accordingly, the silica used for the compounds according to the invention may be adjusted in a tailor-made manner to the required properties of the W-compound to be immobilized. In this regard it is noteworthy that depending on the number of mmol of hydroxyl groups per gram silica, the amount of W compound per gram of silica and ultimately the activity of the resulting catalyst may be adjusted depending upon needs.

In a preferred embodiment, silica is subjected to a temperature in the range of from 400 to 800° C. for a period ranging from 4 to 24 under pressure ranging from $10^{-6}$ mbar to 1 bar. Temperature and pressure may be performed in ramps.

Preferably, hydroxyl content determined by means of titration with MeMgCl ranges from 0.05 mmol to 2.00 mmol per g silica, further preferred from 0.1 mmol to 1 mmol per g silica.

The term "metathesis" refers to alkene(olefin)metathesis.

The term "cross metathesis" encompasses the reaction between two different olefins.

The term "ethenolysis" encompasses the reaction of an olefin having an internal olefinic bond with ethylene.

The term "turnover frequency (TOF)" defines the number of turnovers of moles of olefin per time unit of a certain catalyst.

The term "electron withdrawing" or "electron withdrawing group (EWG)" encompasses a group which draws electrons away from the central W of the compound according to the invention.

The term "electron donating group" or "electron donor" encompasses a group which donates electrons to the central W of the compound according to the invention.

The person skilled in the art is familiar with terms such as "electron withdrawing group (EWG)" or "electron donor" and can residues $R^1$ and $R^5$ attribute to the respective properties.

The term "olefinic double bond" refers to a carbon-carbon double bond or ethylenic double bond in a first olefin and a second olefin.

The term "olefin" as used in the terms "first olefin" and "second olefin" refers to any species having at least one ethylenic double bond such as linear and branched chain aliphatic olefins, cycloaliphatic olefins, or aryl substituted olefins. Olefins may comprise terminal double bond(s) ("terminal olefin") and/or internal double bond(s) ("internal olefin") and can be cyclic or acyclic, linear or branched, optionally substituted. The total number of carbon atoms can be from 2 to 100, or from 2 to 40; the double bonds of a terminal olefin may be mono- or bi-substituted and the double bond of an internal olefin may be bi-, tri-, or tetrasubstituted. In some cases, an internal olefin is bisubstituted.

Non-limiting examples of terminal olefins are substituted and unsubstituted linear alkyl internal olefins such as $C_4$-$C_{30}$ olefins (e.g., 1-butene, 1-pentene, 1-hexene, 1-heptene, 1-octene, 1-decene, 1-dodecene, 1-tetradecene, 1-hexadecene, 1-octadecene, 1-eicosene, allylbenzene, allyltrimethylsilane, methyl-10-undecenoate, allylboronic acid pincol ester, allylbenzylether, N-allyl-4-methylbenzenesulfonamide, allylaniline, methyl-9-decenoate, allyloxy(tert-butyl) dimethyl silane, allylcyclohexane, etc.).

In one embodiment, the olefin having a terminal olefinic double bond is of formula $RCH=CH_2$, wherein R is selected from H, alkyl, alkenyl, aryl, heteroalkyl, heteroalkenyl, heteroaryl, or acyl, optionally substituted.

In one embodiment, the olefin is a polyisoprene.

The term "cyclic olefin" refers to any cyclic species comprising at least one ethylenic double bond in a ring. The atoms of the ring may be optionally substituted. The ring may comprise any number of carbon atoms and/or heteroatoms. In some cases, the cyclic olefin may comprise more than one ring. A ring may comprise at least 3, at least 4, at least 5, at least 6, at least 7, at least 8, or more, atoms. Non-limiting examples of cyclic olefins include norbornene, dicyclopentadiene, bicyclo compounds, oxabicyclo compounds, and the like, all optionally substituted. "Bicyclo compounds" are a class of compounds consisting of two rings only, having two or more atoms in common. "Oxabicyclo compounds" are a class of compounds consisting of two rings only, having two or more atoms in common, wherein at least one ring comprises an oxygen atom.

In another embodiment, the first and the second olefin or the first and the second olefin may bear one or more functional groups.

Preferably, the first and the second olefin or the first or the second olefin may bear one or more functional groups independently selected from the group consisting of ether, ester, amide, amine, halogen, nitrile, thioether, thioester, aryl, or heteroaryl.

In a further preferred embodiment, the first and the second olefin or the first or the second olefin bear one or more functional groups independently selected from alkoxy, aryloxy, perhaloalkoxy, arylalkoxy, heteroaryl, heteroaryloxy, heteroarylalkyl, heteroarylalkoxy, amino, halogen, alkylthio, oxo, carboxy esters, carboxamido, acyloxy, aminoalkyl, alkylaminoaryl, alkylaminoalkyl, alkoxyaryl, arylamino, arylalkylamino, alkylsulfonyl, carboxamidoalkylaryl, carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl.

The term "alkyl" encompasses saturated aliphatic groups, including straight-chain alkyl groups, branched-chain alkyl groups, cycloalkyl (alicyclic) groups, alkyl substituted cycloalkyl groups, and cycloalkyl substituted alkyl groups and alkyl groups substituted with aryl. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. In some embodiments, an alkyl group may be a lower alkyl group, wherein a lower alkyl group comprises 10 or fewer carbon atoms in its backbone (e.g., $C_1$-$C_{10}$ for straight chain lower alkyls).

In one embodiment, the term "alkyl" encompasses $C_1$-$C_4$ alkyl such as methyl, isopropyl iPr) or t-butyl (tBu).

The term "alkyl" also encompasses bridged hydrocarbon residues such as the adamantyl residue, particularly the adamant-1-yl residue.

The term "alkyl" also encompasses anellated ring systems such as the fluorene-9-yl residue such as the 9-phenyl-fluorene-9-yl residue.

The term "t-Bu" denotes a tertiary butyl group $(CH_3)_3C$.

The term "$tBu_{F3}$" denotes a tertiary butyl group $(CF_3)(CH_3)_2C$. The term "$tBu_{F6}$" denotes a tertiary butyl group $(CF_3)_2(CH_3)C$. The term "$tBu_{F9}$" denotes a tertiary butyl group $(CF_3)_3C$.

The term "alkoxy" refers to the group —O-alkyl, wherein alkyl has the meaning as defined above in connection with the term alkyl.

The term "alkenyl" refers to olefinic groups as described above. The alkenyl group may be optionally substituted with the substituents defined above.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated π electron system, while other, adjoining rings can be cycloalkyls, cycloalkenyls, cycloalkynyls, aryls, and/or heterocyclyls. The aryl group may be optionally substituted, as described herein.

The term "carbocyclic aryl groups" as used herein refers to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the aryl groups may include monocyclic carbocyclic aryl groups and polycyclic or fused compounds (e.g., two or more adjacent ring atoms are common to two adjoining rings) such as naphthyl group. Non-limiting examples of aryl groups include phenyl, naphthyl, tetrahydronaphthyl, indanyl, indenyl, and the like.

A preferred aryl residue is 2,6-diisopropylphenyl as residue $R^1$. A further preferred aryl residue is 2,6-dichlorophenyl as residue $R^1$ or pentafluorophenyl, 2-(trifluoromethyl)phenyl or 2,6-di(trifluoromethyl)phenyl.

The term "phenoxy" refers to the group $C_6H_5O$—.

The term "thiophenoxy" or "phenylthio" refers to the group $C_6H_5S$—

This phenoxy or thiophenoxy residue may be substituted with up to five substituents independently selected from alkyl, preferably $C_1$-$C_4$ alkyl such as methyl, isopropyl or t-butyl, alkoxy, preferably $C_1$-$C_4$ alkoxy, phenoxy, phenyl, halogen.

A preferred phenoxy residue is 2,6-diphenylphenoxy as residue $R^5$ or 4-fluoro-2,6-dimesitylphenoxy or 2,6-di-tert.-butylphenoxy 4-bromo-2,6-di-tert.-butylphenoxy or 4-methoxy-2,6-di-tert.-butylphenoxy or 4-methyl-2,6-di-tert.-butylphenoxy or 2,4,6-tri-tert.-butylphenoxy or 2,3,5,6-tetraphenylphenoxy or 4-bromo-2,3,5,6-tetraphenylphenoxy or 2,6-di(4-bromophenyl)-3,5-diphenylphenoxy or 4-bromo-2,6-di(4-bromophenyl)-3,5-diphenylphenoxy.

A preferred thiophenoxy residue is 2,6-diphenylthiophenoxy, 4-bromo-2,6-diphenylthiophenoxy, 4-fluoro-2,6-diphenylthiophenoxy, 4-methyl-2,6-diphenylthiophenoxy, 2,4,6-triphenylthiophenoxy, 4-fluoro-dimesitylthiophenoxy, 2,6-di-tert.-butylthiophenoxy, 4-bromo-2,6-di-tert.-butylthiophenoxy, 4-methoxy-2,6-di-tert.-butylthiophenoxy, 4-methyl-2,6-di-tert.-butylthiophenoxy, 2,4,6-tri-tert.-butylthiophenoxy, 2,3,5,6-tetraphenylthiophenoxy, 4-bromo-2,3,5,6-tetraphenylthiophenoxy, 2,6-di(4-bromophenyl)-3,5-diphenylthiophenoxy, 4-bromo-2,6-di(4-bromophenyl)-3,5-diphenylthiophenoxy as residue $R^5$.

The term "heteroaryl" as used herein refers to aryl groups as described herein in which one or more atoms is a heteroatom (e.g., oxygen, nitrogen, sulfur, and the like), optionally substituted. Examples of aryl and heteroaryl groups include, but are not limited to, phenyl, aryloxy, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like.

A preferred heteroaryl residue as residue $R^5$ is the pyrrol-1-yl residue (py) or 2,5-dimethylpyrrol-1-yl (2,5-$Me_2$py or $Me_2$pyr) or 2,5-diphenylpyrrol-1-yl. The pyrrol-1-moiety is also termed as pyrrolide.

The term "heteroalkyl" refers to alkyl groups as described herein in which one or more atoms is a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "halogen" refers to F, Cl, Br, I.

The term "acyl" refers to H, alkyl, alkenyl, aryl, heteroalkyl and heteroaryl groups as defined above, which are linked to another atom or to another moiety such as a olefinic double bond via a carbonyl group.

The term "triphenylsilyloxy" refers to preferred group $(C_6H_5)_3SiO$, wherein the phenyl residue may be substituted. The term "triphenoxysilyloxy" refers to group $(C_6H_5O)_3SiO$, wherein the phenyl residue may be substituted.

The term "trialkylsilyloxY" refers to preferred group $(C_1-C_4)_3SiO$, wherein the alkyl residue may be substituted. The term "trialkoxysilyloxy" refers to group $(C_1-C_4 O)_3SiO$, wherein the alkoxy residue may be substituted.

The term "comprising" is used in the meaning of "including but not limited to".

The term "consisting" of is used in the meaning "including and limited to".

The term "first or second olefin" is in one embodiment synonymously used with the term "first and second olefin".

The term "chemical reaction" encompasses a reaction in which in a compound a new bond is formed.

The terms "substituted" and "optionally substituted" are contemplated to include all permissible substituents of organic compounds, "Permissible" being in the context of the chemical rules of valence known to those of ordinary skill in the art. Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl.

In one embodiment, the term "$R^6$—CO—$NR^{13}$" means a 4 to 8 membered cyclic carbon- and N-containing ring in which N is linked to M.

The term "N-containing carbon ring" means that the ring contains besides carbon atoms at least one nitrogen atom.

EXAMPLES

1. General Procedures

All experiments were carried out under dry and oxygen free argon atmosphere using either standard Schlenk or glove-box techniques for organometallic synthesis. For the syntheses, reactions were carried out using high vacuum lines ($10^{-5}$ mBar) and glove-box techniques. Pentane, toluene and diethyl ether were purified using double MBraun SPS alumina column, and were degassed using three freeze-pump-thaw cycles before being used. DME and THF were distilled from Na/Benzophenone. Silica (Aerosil Degussa, 200 $m^2g^{-1}$) was compacted with distilled water, calcined at 500° C. under air for 4 h and treated under vacuum ($10^{-5}$ mBar) at 500° C. for 12 h and then at 700° C. for 4 h (support referred to as $SiO_{2-(700)}$ and contained 0.26 mmol of OH per g as measured by titration with MeMgCl. All infrared (IR) spectra were recorded using a Bruker spectrometer placed in the glovebox, equipped with OPUS software. A typical experiment consisted in the measurement of transmission in 32 scans in the region from 4000 to 400 $cm^{-1}$. The $^1H$ and $^{13}C$-NMR spectra were obtained on Bruker DRX 200, DRX 250 or DRX 500 spectrometers. The solution spectra were recorded in $C_6D_6$ at room temperature. The $^1H$ and $^{13}C$ chemical shifts are referenced relative to the residual solvent peak. Compounds [W(NAr)(CHCMe$_3$)(OtBu)$_2$],[1] [W(NAr)(CHCMe$_3$)(OtBu$_{F3}$)$_2$],[1] [W(NAr)(CHCMe$_3$)(OtBu$_{F6}$)$_2$],[1] [W(NAr$_{Cl}$)(CHCMe$_2$Ph)(Me$_2$Pyr)$_2$],[2] [W(NAr$_{Cl}$)(CHCMe$_3$)(OtBu$_{F6}$)$_2$],[2] [Mo(NAr$_{Cl}$)(CHCMe$_2$Ph)(Me$_2$Pyr)$_2$],[3] [(≡SiO)W(NAr)(CHCMe$_3$)(Me$_2$Pyr)],[4] [(≡SiO)Mo(NAr)(CHCMe$_3$)(Me$_2$Pyr)],[5] and [(≡SiO)Mo(NAr)(CHCMe$_3$)(OtBu$_{F6}$)][6] were synthesized according to literature procedures. Further precursors or starting materials may be prepared according to such procedures or according to methods specified in the following.

[1] Schrock, R. R.; De Pue, R. T.; Feldman, J.; Yap, K. B.; Yang, D. C.; Davis, W. M.; Park, L.; Dimare, M.; Schofield, M.; Anhaus, J.; Walborsky, E.; Evitt, E.; Krüger, C.; Betz, P. *Organometallics* 1990, 2262.

[2] Arndt, S.; Schrock, R. R.; Müller, P. *Organometallics* 2007, 1279.

[3] Schrock, R. R.; Jamieson, J. Y.; Dolman, S. J.; Miller, S. A.; Bonitatebus, P. J., Jr.; Hoveyda, A. H. *Organometallics* 2002, 21, 409.

[4] Blanc, F.; Berthoud, R.; Coperet, C.; Lesage, A.; Emsley, L.; Singh, R.; Kreickmann, T.; Schrock, R. R. *Proc. Nat. Acad. Sci.* 2008, 12123.

[5] Blanc, F.; Thivolle-Cazat, J.; Basset, J M.; Coperet, C. *Chem. Eur. J.* 2008, 9030.

[6] Rendon, N.; Berthoud, R.; Blanc, F.; Gajan, D.; Maishal, T.; Basset, J M.; Copéret, C.; Lesage, A.; Emsley, L.; Marinescu, S. C.; Singh, R.; Schrock, R. R. *Chem. Eur. J.* 2009, 5083.

Abbreviations:
THF=tetrahydrofuran
DME=1,2-dimethoxyethane
Et$_2$O=diethyl ether
TfOH=trifluoromethanesulfonic acid
LiMe$_2$Pyr=lithium 2,5-dimethylpyrrolide 2. Syntheses
2.1 Synthesis of Precursors:

Precursor Example 1: [W(NAr)(CHCMe$_3$)(OtBu$_{F9}$)$_2$], Ar=2,6-iPr$_2$C$_6$H$_3$ A cold (−40° C.) suspension of $(CF_3)_3COLi$ (148 mg, 0.61 mmol, 2 equiv.) in diethyl ether (2 mL) was added to a solution of 250 mg of [W(NAr)(CHCMe$_3$)(OTf)$_2$(DME)] (0.305 mmol, 1.05 equiv.) in cold diethyl ether (6 mL, −40° C.) while stirring. The dark red solution was stirred for 2 h at room temperature, and the volatiles were removed under reduced pressure. The dark red solid was suspended in pentane (4 mL) and filtered on Celite® to afford a clear orange solution. The filtrate was taken to dryness in vacuo, and the orange powder dissolved back in pentane (2 mL). This drying/dissolution cycle was repeated four consecutive times, in order to remove all the coordinated DME molecules. Finally, the orange powder was solubilized in a minimum amount of pentane, and stored at −40° C. to give orange crystals, that were washed with cold (−40° C.) pentane, affording after drying in vacuo 218 mg of [W(NAr)(CHCMe$_3$)(OtBu$_{F9}$)$_2$] (0.21 mmol, 69%). $^1H$ NMR (200 MHz, C$_6$H$_6$) δ (ppm) 9.45 (s, 1H, CHCMe$_3$), 7.04-6.94 (m, 3H, Ar), 3.46 (2H, sep-tet, CHMe$_2$), 1.15 (d, 12H, CHMe$_2$), 1.06 (s, 9H, CHCMe$_3$). $^{19}F$ NMR (200 MHz, C$_6$D$_6$) δ (ppm) −73.1 (s, 18F, C(CF$_3$)).

Precursor Example 2: [W(NAr$_{Cl}$)(CHCMe$_2$Ph)(OtBu$_{F9}$)$_2$(DME)], Ar$_{Cl}$=2,6-Cl—C$_6$H$_3$ A cold (−40° C.) suspension of $(CF_3)_3COLi$ (162.4 mg, 0.67 mmol, 2 equiv.) in diethyl ether (4 mL) was added to a suspension of 250 mg of [W(NAr$_{Cl}$)(CHCMe$_2$Ph)(OTf)$_2$(DME)] (0.33 mmol, 1 equiv.) in cold diethyl ether (6 mL, −40° C.) while stirring. The dark brown reaction mixture was stirred for 1.5 h at room temperature, and the volatiles were removed under reduced pressure, affording a light brown solid. The solid was extracted in pentane (15 mL), filtered on Celite® and rinsed with pentane (2×5 mL). The volume of the filtrate was reduced to ca. 2 mL in vacuo and was stored at −40° C., affording an orange powder. The powder was filtered and rinsed with cold (−40° C.) pentane (2×1 mL) to afford after drying in vacuo 165.2 mg of an orange powder of the title compound (0.159 mmol, 48%). Single crystals suitable diffraction studies of [W(NAr$_{Cl}$)(CHCMe$_2$Ph)(OtBu$_{F9}$)$_2$] were grown in −40° C. toluene. $^1$H NMR (300 MHz, C$_6$H$_6$) δ (ppm) 9.61 (s, 1H, CHCMe$_3$), 7.45 (m, 2H, Ph), 7.00 (m, 2H, Ph), 6.74 (m, 1H, Ph), 6.69 (d, 2H, Ar, J=8.1 Hz), 6.19 (t, 1H, Ar, J=8.2 Hz), 3.00 (s, 6H, DME), 2.87 (s, 4H, DME), 1.44 (s, 6H, CHCMe$_2$Ph). $^{19}$F NMR (300 MHz, C$_6$D$_6$) δ (ppm) −73.1 (s, 18F, C(CF$_3$)).

Precursor Example 3: [W(NAr$_{Cl}$)(CHCMe$_2$Ph)(OtBu)$_2$], Ar$_{Cl}$=2,6-Cl—C$_6$H$_3$ To a cold THF solution (−41° C., 20 mL) of [W(NAr$_{Cl}$)(CHCMe$_2$Ph)(Me$_2$Pyr)$_2$] (200 mg, 0.30 mmol, 1 equiv.) was added dropwise over 1h a solution of tBuOH (44.6 mg, 0.60 mmol, 2 equiv.) in cold THF (−41° C., 10 mL). The resulting brown solution was further stirred overnight in the MeCN/CO$_2$ bath, slowly reaching room temperature. The resulting dark brown solution was dried in vacuo (2 h, 10$^{-2}$ mBar). The brown residue was extracted in cold pentane (−40° C., 3 mL), filtered on Celite® and evaporated to dryness to afford 108 mg of an oily orange solid (0.173 mmol, 57%). $^1$H NMR (300 MHz, C$_6$H$_6$) δ (ppm) 8.09 (s, 1H, CHCMe$_2$Ph), 7.54 (m, 2H, Ph), 7.16 (m, 2H, Ph), 7.08 (m, 1H, Ph), 6.97 (m, 2H, Ar$_{Cl}$), 6.31 (t, 1H, Ar$_{Cl}$, J=8.2 Hz), 1.72 (s, 6H, CHCMe$_2$Ph), 1.26 (s, 18H, OCMe$_3$).

Precursor Example 4: [W(NAr$_{CF3}$)(CHCMe$_2$Ph)(Me$_2$Pyr)$_2$], (Ar$_{CF3}$=2-CF$_3$—C$_6$H$_4$, Me$_2$Pyr=2,5-dimethylpyrrolide)

A cold suspension of 47.5 mg of LiMe$_2$Pyr (0.47 mmol, 2 equiv.) in toluene (−40° C., 3 mL) was added dropwise under stirring to a cold toluene solution (−40° C., 8 mL) of [W(NAr$_{CF3}$)(CHCMe$_2$Ph)(OTf)$_2$(DME)] (203 mg, 0.23 mmol, 1 equiv.). The suspension was stirred overnight, affording an orange solution and an off-white precipitate. The solution was filtered on Celite®, affording a clear orange solution, and taken to dryness to yield a dark orange oil. This oil was triturated with cold (−40° C.) pentane (2×1.5 mL) to afford after drying in vacuo 108 mg of a light yellow powder (0.16 mmol, 69%). $^1$H NMR (300 MHz, C$_6$H$_6$) δ (ppm) 10.96 (s, 1H, CHCMe$_2$Ph), 7.33 (m, 2H, Ph), 7.20-6.87 (m, 6H, Ph-Ar$_{CF3}$), 6.75 (m, 1H, Ph), 6.52 (t, 1H, Ar$_{CF3}$, J=8.0 Hz), 6.02 (br s, 6H, Me$_2$Pyr), 2.11 (br s, 12H, Me$_2$Pyr), 1.58 (s, 6H, CHCMe$_2$Ph). $^{19}$F NMR (200 MHz, C$_6$D$_6$) δ (ppm) −60.4 (s, 3F, CF$_3$).

2.2 Synthesis of Supported Catalysts

Example 1: [(≡SiO)W(NAr)(CHCMe$_3$)(OtBu)] (Ar=2,6-iPr$_2$C$_6$H$_3$) (Representative Procedure)

A solution of 104 mg of [W(NAr)(CHCMe$_3$)(OtBu)$_2$] (0.181 mmol, 1.05 equiv.) in benzene (2 mL) was added to a suspension of SiO$_{2-(700)}$ (673 mg, 0.17 mmol) in benzene (2 mL) at room temperature. The suspension was slowly stirred at room temperature for 12 h, resulting in a fading of the color of the solution and a coloration of the silica to yellow. The yellow solid was collected by filtration, and was washed by four suspension/filtration cycles in benzene (4×2 mL). The resulting yellow solid was dried thoroughly under high vacuum (10$^{-5}$ mBar) at room temperature for 3 h to afford 672 mg of the title compound. All the filtrate solutions were collected and analyzed by $^1$H NMR spectroscopy in C$_6$D$_6$ using ferrocene as internal standard (33.7 mg, 1.05 equiv.), indicating that 0.07 mmol of tBuOH were released upon grafting (0.4 tBuOH/W$_{surf}$). Elemental Analysis: W, 3.32%, C, 4.78%, H, 0.68%, N, 0.48% corresponding to 22 C/W (21 expected), 37.4 H/W (36 expected), 1.9 N (1 expected).

Example 2: [(≡SiO)W(NAr)(CHCMe$_3$)(OtBu$_{F3}$)] (Ar=2,6-iPr$_2$C$_6$H$_3$, tBu$_{F3}$OH=(CF$_3$)Me$_2$COH)

From a solution of [W(NAr)(CHCMe$_3$)(OtBu$_{F3}$)$_2$(DME)] and a suspension of SiO$_{2-(700)}$ (500 mg, 0.13 mmol) in benzene (2 mL) 552 mg of a yellow solid were isolated. All the filtrate solutions were collected and analysed by $^1$H NMR spectroscopy in C$_6$D$_6$ using ferrocene as internal standard (11 mg, 1 equiv.), indicating that 0.11 mmol of tBu$_{F3}$OH were released upon grafting (0.85 tBu$_{F3}$OH/W$_{surf}$). Elemental Analysis: W, 3.71%, C, 5.18%, H, 0.72%, N, 0.38% F, 1.09% corresponding to 21.4 C/W (21 expected), 35.4 H/W (33 expected), 1.3 N (1 expected).

Example 3: [(≡SiO)W(NAr)(CHCMe$_3$)(OtBu$_{F6}$)] (Ar=2,6-iPr$_2$C$_6$H$_3$, tBu$_{F6}$OH=(CF$_3$)$_2$MeCOH)

From a solution of 100 mg of [W(NAr)(CHCMe$_3$)(OtBu$_{F6}$)$_2$] (0.13 mmol, 1.05 equiv.) in benzene (3 mL) and a suspension of SiO$_{2-(700)}$ (500 mg, 0.12 mmol) in benzene (2 mL), 512 mg of a light orange solid were isolated. All the filtrate solutions were collected and analysed by $^1$H NMR spectroscopy in C$_6$D$_6$ using ferrocene as internal standard (11.8 mg, 0.5 equiv.), indicating that 0.10 mmol of tBu$_{F6}$OH were released upon grafting (0.8 tBu$_{F6}$OH/W$_{surf}$). Elemental Analysis: W, 3.88%, C, 5.39%, H, 0.65%, N, 0.37%, F, 2.05% corresponding to 21.3 C/W (21 expected), 30.6 H/W (30 expected), 1.3 N (1 expected).

Example 4: [(≡SiO)W(NAr)(CHCMe$_3$)(OtBu$_{F9}$)] (Ar=2,6-iPr$_2$C$_6$H$_3$, tBu$_{F9}$OH=(CF$_3$)$_3$COH)

From a solution of 185.9 mg of [W(NAr)(CHCMe$_3$)(OtBu$_{F}$g)$_2$] (0.21 mmol, 1.05 equiv.) in benzene (4 mL) and a suspension of SiO$_{2-(700)}$ (790 mg, 0.12 mmol) in benzene (3 mL) 857 mg of an orange solid were isolated. Elemental Analysis: W, 3.47%, C, 4.84%, H, 0.51%, N, 0.38%, F, 3.14% corresponding to 21.3 C/W (21 expected), 26.8 H/W (27 expected), 1.4 N (1 expected).

Example 5: [(≡SiO)W(NAr$_{Cl}$)(CHCMe$_2$Ph)(Me$_2$Pyr)] (Ar$_{Cl}$=2,6-Cl—C$_6$H$_3$, Me$_2$Pyr=2,5-dimethylpyrrolide)

From a solution of 138 mg of [W(NAr$_{Cl}$)(CHCMe$_2$Ph)(Me$_2$Pyr)$_2$] (0.21 mmol, 1.05 equiv.) in benzene (3 mL) and a suspension of SiO$_{2-(700)}$ (800 mg, 0.20 mmol) in benzene (2 mL) 790 mg of a light brown solid were isolated. All the filtrate solutions were collected and analyzed by $^1$H NMR spectroscopy in C$_6$D$_6$ using ferrocene as internal standard (38.7 mg, 1 equiv.), indicating that 0.13 mmol of Me$_2$PyrH were released upon grafting (0.7 Me$_2$PyrH/W$_{surf}$).

Example 6: [(≡SiO)W(NAr$_{Cl}$)(CHCMe$_2$Ph)(OtBu$_{F6}$)], (Ar$_{Cl}$=2,6-Cl—C$_6$H$_3$, tBu$_{F6}$OH=(CF$_3$)$_2$MeCOH))

From a solution of 101 mg of [W(NAr$_{Cl}$)(CHCMe$_3$)(OtBu$_{F6}$)$_2$] (0.13 mmol, 1.05 equiv.) in benzene (2 mL) and a suspension of $SiO_{2-(700)}$ (463 mg, 0.12 mmol) in benzene (2 mL), 450 mg of a light orange solid were isolated. All the filtrate solutions were collected and analysed by $^1$H NMR spectroscopy in $C_6D_6$ using ferrocene as internal standard (22.3 mg, 1 equiv.), indicating that 0.08 mmol of $tBu_{F6}OH$ were released upon grafting (0.7 $tBu_{F6}OH/W_{surf}$).

Example 7: [($\equiv$SiO)W(NAr$_{Cl}$)(CHCMe$_2$Ph)(OtBu$_{F9}$)], (Ar$_{Cl}$=2,6-Cl—C$_6$H$_3$, tBu$_{F9}$OH=(CF$_3$)$_3$COH))

From a solution of 98.5 mg of [W(NAr$_{Cl}$)(CHCMe$_2$Ph)(OtBu$_{F9}$)$_2$(DME)] (0.10 mmol, 1.05 equiv.) in benzene (2 mL) and a suspension of $SiO_{2-(700)}$ (365 mg, 0.09 mmol) in benzene (2 mL) 360 mg of a light orange solid were obtained. All the filtrate solutions were collected and analysed by $^1$H NMR spectroscopy in $C_6D_6$ using ferrocene as internal standard (17.7 mg, 1 equiv.), indicating that 0.09 mmol of DME were released upon grafting (0.9 DME/$W_{surf}$).

Example 8: [($\equiv$SiO)W(NAr$_{CF3}$)(CHCMe$_2$Ph)(Me$_2$Pyr)] (Ar$_{CF3}$=2-CF$_3$—C$_6$H$_4$, Me$_2$Pyr=2,5-dimethylpyrrolide)

From a solution of 75 mg of [W(NAr$_{CF3}$)(CHCMe$_2$Ph)(Me$_2$Pyr)$_2$] (0.11 mmol, 1.05 equiv.) in benzene (3 mL) and a suspension of $SiO_{2-(700)}$ (403 mg, 0.10 mmol) in benzene (2 mL), 390 mg of a yellow solid were isolated. All the filtrate solutions were collected and analysed by $^1$H NMR spectroscopy in $C_6D_6$ using ferrocene as internal standard (38.7 mg, 1 equiv.), indicating that 0.09 mmol of Me$_2$PyrH were released upon grafting (0.95 Me$_2$PyrH/$W_{surf}$).

Example 9: [($\equiv$SiO)W(NAr$_{Cl}$)(CHCMe$_2$Ph)(OtBu)] Ar$_{Cl}$=2,6-Cl—C$_6$H$_3$ A solution of 100 mg of [W(NAr$_{Cl}$)(CHCMe$_2$Ph)(OtBu)$_2$] (0.16 mmol, 1.05 equiv.) in cold toluene (2 mL, −40° C.) was added to a suspension of $SiO_{2-(700)}$ (576 mg, 0.15 mmol) in cold toluene (2 mL, −40° C.). The suspension was slowly stirred at room temperature for 30 min, resulting in a fading of the color of the solution and a coloration of the silica to orange. The orange solid was collected by filtration, and was washed by four suspension/filtration cycles in benzene (4×2 mL). The resulting orange solid was dried thoroughly under high vacuum ($10^{-5}$ mBar) at room temperature for 5 h to afford 110 mg of the title compound. All the filtrate solutions were collected and analysed by $^1$H NMR spectroscopy in $C_6D_6$ using ferrocene as internal standard (27.9 mg, 1 equiv.), indicating that 0.12 mmol of tBuOH were released upon grafting (0.8 tBuOH/$W_{surf}$).

Example 10: [($\equiv$SiO)Mo(NAr$_{Cl}$)(CHCMe$_2$Ph)(Me$_2$Pyr)] (Ar$_{Cl}$=2,6-Cl—C$_6$H$_3$, Me$_2$Pyr=2,5-dimethylpyrrolide)

From a solution of 113 mg of [Mo(NAr$_{Cl}$)(CHCMe$_2$Ph)(Me$_2$Pyr)$_2$] (0.20 mmol, 1.05 equiv.) in benzene (3 mL) and a suspension of $SiO_{2-(700)}$ (710 mg, 0.19 mmol) in benzene (2 mL), 690 mg of a red solid were isolated. All the filtrate solutions were collected and analyzed by $^1$H NMR spectroscopy in $C_6D_6$ using ferrocene as internal standard (34.5 mg, 1 equiv.), indicating that 0.14 mmol of Me$_2$PyrH were released upon grafting (0.75 Me$_2$PyrH/$W_{surf}$).

Example 11: [($\equiv$SiO)Mo(NAr)(CHCMe$_3$)(OC(CF$_3$)$_2$Ph)] (Ar=2,6-iPr$_2$C$_6$H$_3$)

From a solution of 125 mg of [W(NAr)(CHCMe$_3$)(OC(CF$_3$)$_2$Ph)$_2$] (0.14 mmol, 1.05 equiv.) in benzene (3 mL) and a suspension of $SiO_{2-(700)}$ (510 mg, 0.13 mmol) in benzene (2 mL), 517 mg of a yellow green solid were isolated. All the filtrate solutions were collected and analyzed by $^1$H NMR spectroscopy in $C_6D_6$ using ferrocene as internal standard (26.0 mg, 1 equiv.), indicating that 0.12 mmol of HOC(CF$_3$)$_2$Ph were released upon grafting (0.9 HOC(CF$_3$)$_2$Ph/$W_{surf}$).

Example 12: [($\equiv$SiO)Mo(NAr)(CHCMe$_2$Ph)(OtBu$_{F6}$)] (Ar=2,6-iPr$_2$C$_6$H$_3$)

(N. Rendon et. al., Chem. Eur. J. 2009, 15, 5083-5089)

Example 13: [($\equiv$SiO)W(NAr)(CHCMe$_2$Ph)(OSiPh$_3$)] (Ar=2,6-iPr$_2$C$_6$H$_3$)

From a solution of 241 mg of [W(NAr)(CHCMe$_2$Ph)(OSiPh$_3$)$_2$] (0.21 mmol, 1.05 equiv.) in benzene (4 mL) and a suspension of $SiO_{2-(700)}$ (810 mg, 0.23 mmol) in benzene (2 mL), a light orange solid were isolated. All the filtrate solutions were collected and analyzed by $^1$H NMR spectroscopy in $C_6D_6$ using ferrocene as internal standard (52.3 mg, 1.33 equiv.), indicating that 0.48 mmol of HOSiPh$_3$ were released upon grafting.

Example 14: [($\equiv$SiO)W(NAr)(CHCMe$_3$)(Me$_2$Pyr)] (Ar=2,6-iPr$_2$C$_6$H$_3$)

(F. Blanc et al., Proc. Nat. Acad. Sci. 2008, 12123)

Example 15: [($\equiv$SiO)Mo(NAr)(CHCMe$_2$Ph)(Me$_2$PYr)] (Ar=2,6-iPr$_2$C$_6$H$_3$)

(F. Blanc et al., J. Amer. Chem. Soc. 2007, 129, 8434-8435)

Example 16: [($\equiv$SiO)W(NAr$_{F5}$)(CHCMe$_2$Ph)(Me$_2$Pyr)] (Ar$_{F5}$=C$_6$F$_5$)

From a solution of 59 mg of [W(NC$_6$F$_5$)(CHCMe$_2$Ph)(Me$_2$Pyr)$_2$] (0.086 mmol, 1.05 equiv.) in benzene (3 mL) and a suspension of $SiO_{2-(700)}$ (314 mg, 0.082 mmol) in benzene (3 mL), 343 mg of a orange-yellow solid were isolated. All the filtrate solutions were collected and analyzed by $^1$H NMR spectroscopy in $C_6D_6$ using ferrocene as an internal standard, indicating that 0.07 mmol of Me$_2$PyrH were released upon grafting (0.9 Me$_2$PyrH/$W_{surf}$). Elemental Analysis: W, 4.13%, C, 5.95%, H, 0.48%, N, 0.77% F, 2.17% corresponding to 22.1 C/W (22 expected), 21.2 H/W (20 expected), 2.4 N (2 expected), 5.1 F (5 expected).

Example 17: [($\equiv$SiO)W(NAr)(CHCMe$_2$Ph)(OAr$_{F5}$)] (Ar=2,6-iPr$_2$C$_6$H$_3$) (Ar$_{F5}$=C$_6$F$_5$)

3. Catalytic Activity
3.1 Ethenolysis of 9-octadecene:
9-Octadecene (E/Z isomer mixture) was purified by fractional distillation under inert atmosphere at reduced pressure (1 mbar) then it was percolated through a column of activated aluminum oxide 90 (basic, Brockman I, dried at 300° C. under 0.1 mbar vacuum for 24 h; column: d=4 cm, l=15 cm for 1 L of 9-octadecene) and was kept under inert atmosphere.

In a nitrogen gas filled glove-box the calculated amount (0.5-5 mL) of 9-octadecene was added to the silica supported catalyst (3-5 mg) measured into a 30 ml glass vial. The vial was placed into a stainless steel autoclave and the reaction mixture was stirred by a magnetic stir bar under 10 atm of ethylene overpressure at room temperature for the specified time (see results table). The excess of ethylene was let out from the autoclave, the reaction mixture was quenched by wet ethyl acetate and the reaction mixture was analyzed by GC-FID (Shimadzu GC-2010 Plus; Zebron ZB-35HT Inferno).

The subsequent table summarizes the results obtained with selected catalysts:

| Catalyst (0.01 mol % W or Mo) | Conversion (%) (14 h) |
| --- | --- |
| Example 2: [(≡SiO)W(NAr)(CHCMe$_3$)(OtBu$_{F3}$)] | 41.8 |
| Example 5: [(≡SiO)W(NAr$_{Cl}$)(CHCMe$_2$Ph)(Me$_2$Pyr)] | 25.7 |
| Example 12: [(≡SiO)Mo(NAr)(CHCMe$_2$Ph)(OtBu$_{F6}$)] | 37.3 |
| Example 12: [(≡SiO)Mo(NAr)(CHCMe$_2$Ph)(OtBu$_{F6}$)] (loading 0.1 mol %) | 54.7 |
| Example 15: [(≡SiO)Mo(NAr)(CHCMe$_2$Ph)(Me$_2$Pyr)] | 53.9 |
| Example 8: [(≡SiO)W(NAr$_{CF3}$)(CHCMe$_2$Ph)(Me$_2$Pyr)] | 39.5 |
| Example 10: [(≡SiO)Mo(NAr$_{Cl}$)(CHCMe$_2$Ph)(Me$_2$Pyr)] | 70.1 |

3.2 Ethenolysis of a Triglyceride (Rape-Seed Oil)

Commercially available edible grade rapeseed oil sample (1 mL) was treated by 6.5 mol % triethylaluminium. Then 0.1 mol-% of the grafted silica catalyst was added. The reaction mixture was stirred in a stainless steel autoclave under 10 bar of ethylene atmosphere at 50° C. for 16 hours. To the reaction mixture sodium methylate in methanol (0.5 M, 20 mL) was added and the mixture was stirred at room temperature for 3 hours. After the end of the transesterification an aliquot (2 mL) was let through a small (7 mL) column of silica gel and the column was washed by tetrahydrofurane (25 mL). The combined elute was analyzed by GCMS-FID using heptadecane as internal standard. The resulting yield relates to methyl decenoate which has been formed in the transesterification reaction.

| Catalyst | Conversion (%) | Yield of methyl decenoate (%) |
| --- | --- | --- |
| Example 8: [(≡SiO)W(NAr$_{CF3}$)(CHCMe$_2$Ph)(Me$_2$Pyr)] | 34 | 16 |
| Example 16: [(≡SiO)W(NAr$_{F5}$)(CHCMe$_2$Ph)(Me$_2$Pyr)] | 66 | 38 |

The invention claimed is:

1. A method of forming an olefin from a first olefin and a second olefin in a metathesis reaction, comprising step (i):
   (i) reacting the first olefin with the second olefin in the presence of a silica supported Mo-alkylidene or W-alkylidene catalyst, wherein the catalyst is of formula I

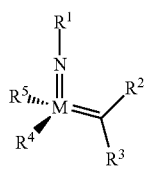

I wherein
M is W or Mo;
$R^1$ is H, aryl, heteroaryl, alkyl, or heteroalkyl, optionally substituted, respectively;
$R^2$ and $R^3$ can be the same or different and are alkyl, alkenyl, heteroalkyl, heteroalkenyl, aryl, or heteroaryl, optionally substituted, respectively, or hydrogen;
$R^5$ is a residue $R^6$—X—, wherein
   $R^6$ is alkyl, aryl, heteroalkyl, heteroaryl, optionally substituted, respectively; ($R^7$, $R^8$, $R^9$)Si; wherein $R^7$, $R^8$, $R^9$ are independently alkyl, alkoxy, phenyl or phenoxy, optionally substituted, respectively; ($R^{10}$, $R^{11}$, $R^{12}$)C, wherein $R^{10}$, $R^{11}$, $R^{12}$ are independently phenyl, alkyl, optionally substituted, respectively;
   X=O, S, or $NR^{13}$, wherein $R^{13}$ is H; or alkyl or aryl, optionally substituted, respectively; or
$R^5$ is $R^6$—CO—$NR^{13}$, wherein $R^6$ and $NR^{13}$ have the meaning as defined above, or wherein $R^6$ and $R^{13}$ taken together form a carbon chain having from 2 to 6 carbon atoms; or
$R^5$ is an optionally substituted 4 to 8 membered N-containing ring, wherein N is linked to M; and
$R^4$ is a residue O—Si(O—)$_3$, and represents silica to which M is linked forming a M-O—Si(O—)$_3$ moiety, and
wherein the first olefin and the second olefin are different from one another.

2. The method of claim 1, wherein
(a) the first olefin is a cyclic olefin and the second olefin is a cyclic olefin; or
(b) the first olefin is a cyclic olefin and the second olefin is a non-cyclic olefin; or
(c) the first olefin is a non-cyclic olefin and the second olefin is a non-cyclic olefin.

3. The method of claim 1, wherein the first olefin or the second olefin is a $C_4$-$C_{30}$ olefin.

4. The method of claim 1, wherein the first olefin has an internal olefinic double bond and the second olefin is ethylene.

5. The method of claim 1, wherein
$R^1$ is aryl or adamant-1-yl, optionally substituted, respectively;
$R^2$ is —C(CH$_3$)$_2$C$_6$H$_5$ or —C(CH$_3$)$_3$;
$R^3$ is H;
$R^5$ is a residue $R^6$—X—, wherein
   X=O and $R^6$ is phenyl or phenyl substituted with up to five substituents independently selected from alkyl; alkoxy; phenoxy, phenyl, optionally substituted, respectively; or halogen; or
   X=S and $R^6$ is phenyl or phenyl substituted with up to five substituents independently selected from alkyl; alkoxy; phenoxy, phenyl, optionally substituted, respectively; or halogen; or
   X=O and $R^6$ is triphenylsilyl or triphenoxysilyl, optionally substituted, respectively; or tri(C$_1$-C$_4$ alkyl)silyl or tri(C$_1$-C$_4$ alkoxy)silyl;
   X=O and $R^6$ is triphenylmethyl, optionally substituted; or
   X=O and $R^6$ is 9-phenyl-fluorene-9-yl; or
   X=O and $R^6$ is 2-phenyl-1,1,1,3,3,3-hexafluoro-prop-2-yl [(C$_6$H$_5$)(CF$_3$)$_2$C]; or
   X=O and $R^6$ is t-butyl, optionally substituted with one or more F groups.

6. The method of claim 1, wherein
$R^1$ is phenyl or phenyl substituted with up to five substituents independently selected from C$_1$-C$_4$ alkyl, $C_1$-$C_4$ alkoxy, $CF_3$, F, Cl, Br or phenyl or phenoxy, optionally substituted, respectively; and X=O and $R^6$ is phenyl substituted with up to five substituents independently selected from $C_1$-$C_4$ alkyl, $C_1$-$C_4$ alkoxy, phenoxy, phenyl, halogen; or X=S and $R^6$ is phenyl substituted with up to five substituents independently selected from $C_1$-$C_4$ alkyl, $C_1$-$C_4$ alkoxy, phenoxy, phenyl, halogen; or X=O and $R^6$ is triphenylsilyl, triphenoxysilyl, tri($C_1$-$C_4$ alkyl)silyl or tri($C_1$-$C_4$ alkoxy)silyl; or X=O and $R^6$ is t-butyl or $(CF_3)(CH_3)_2C$, $(CF_3)_2(CH_3)C$, $(CF_3)_3C$ or $(C_6H_5)(CF_3)_2C$; or $R^5$ is pyrrol-1-yl, 2,5-dimethylpyrrol-1-yl, or 2,5-diphenylpyrrol-1-yl.

7. The method of claim 1, wherein $R^1$ is an electron donating group and $R^5$ is an electron withdrawing group.

8. The method of claim 7, wherein
$R^1$=phenyl substituted with up to five substituents independently selected from $C_1$-$C_4$ alkyl, $C_1$-$C_4$ alkoxy, phenyl, or phenoxy;
$R^2$ is —$C(CH_3)_2C_6H_5$ or —$C(CH_3)_3$;
$R^3$ is H;
$R^5$ is t-$(CF_3)(CH_3)_2CO$, t-$(CF_3)_2(CH_3)CO$, t-$(CF_3)_3CO$, 2-phenyl-1,1,1,3,3,3-hexafluoro-prop-2-yloxy, pyrrol-1-yl, 2,5-dimethylpyrrol-1-yl, or 2,5-diphenylpyrrol-1-yl.

9. The method of claim 1, wherein $R^1$ is an electron withdrawing group and $R^5$ is an electron donating group.

10. The method of claim 1, wherein
$R^1$ is phenyl substituted with up to five substituents independently selected from $CF_3$, F, Cl, or Br;
$R^2$ is —$C(CH_3)_2C_6H_5$ or —$C(CH_3)_3$;
$R^3$ is H;
$R^5$ is t-$(CH_3)_3CO$, tri($C_1$-$C_4$)silyloxy, or tri(phenyl)silyloxy, phenoxy or phenylthio, wherein the phenyl moiety may be substituted with up to five substituents independently selected from $C_1$-$C_4$ alkyl, $C_1$-$C_4$ alkoxy, phenoxy, phenyl, or halogen.

11. The method of claim 1, wherein both $R^1$ and $R^5$ are electron withdrawing groups.

12. The method of claim 1, wherein
$R^1$ is phenyl substituted with up to five substituents independently selected from $CF_3$, F, Cl, or Br;
$R^2$ is —$C(CH_3)_2C_6H_5$ or —$C(CH_3)_3$;
$R^3$ is H;
$R^5$ is $(CF_3)(CH_3)_2CO$, $(CF_3)_2(CH_3)CO$, $(CF_3)_3CO$, $(C_6H_5)(CF_3)_2CO$, pyrrol-1-yl, 2,5-dimethylpyrrol-1-yl, or 2,5-diphenylpyrrol-1-yl.

13. The method of claim 1, wherein M is W.

* * * * *

UNITED STATES PATENT AND TRADEMARK OFFICE
CERTIFICATE OF CORRECTION

PATENT NO. : 10,071,950 B2  
APPLICATION NO. : 14/903119  
DATED : September 11, 2018  
INVENTOR(S) : Georg Emil Frater et al.

Page 1 of 1

It is certified that error appears in the above-identified patent and that said Letters Patent is hereby corrected as shown below:

In the Specification

Column 9, Line 65, delete "... [W(NArc$_{c1}$) ..." and insert --... [W(NAr$_{C1}$) ...--

Column 12, Line 42, delete "... (OtBu$_{Fg}$)$_2$] ..." and insert --... (OtBu$_{F9}$)2] ...--

Signed and Sealed this  
Twenty-second Day of January, 2019

Andrei Iancu  
*Director of the United States Patent and Trademark Office*